United States Patent [19]

Popovich et al.

[11] Patent Number: 4,673,385
[45] Date of Patent: Jun. 16, 1987

[54] PERITONEAL MEMBRANE PLASMAPHERESIS

[76] Inventors: Robert P. Popovich, 2928 Kassarine Pass, Austin, Tex. 78704; Jack W. Moncrief, 3633 W. Lake, Austin, Tex. 78746

[21] Appl. No.: 946,104

[22] Filed: Dec. 22, 1986

Related U.S. Application Data

[63] Continuation of Ser. No. 874,793, Jun. 13, 1986, abandoned, which is a continuation of Ser. No. 817,155, Jan. 7, 1986, abandoned, which is a continuation of Ser. No. 540,010, Oct. 7, 1983, abandoned.

[51] Int. Cl.$^4$ .............................................. A61M 1/00
[52] U.S. Cl. ........................................ 604/28; 604/29
[58] Field of Search ....................... 604/28, 29, 48, 49

[56] References Cited

U.S. PATENT DOCUMENTS 4,133,891  1/1979  Nolph ............................... 604/28 X

OTHER PUBLICATIONS

Yium et al., "Peritoneal Dialysis in the Treatment of Renal Failure in Multiple Myeloma", Southern Medical Journal, Nov. 1971, vol. 64, No. 11, pp. 1403-1405.
Anderson et al. "Treatment of Psoriasis by Peritoneal Dialysis", Health Services Research Center/Health Care Technology Center, University of Missouri, Oct. 1979.

*Primary Examiner*—W. J. Shine
*Attorney, Agent, or Firm*—Arnold, White & Durkee

[57] ABSTRACT

A process to remove large molecules from the body involves infusion of a plasmate solution containing a vasodialating drug into the peritoneal cavity and subsequent drainage on a prescribed schedule.

6 Claims, No Drawings

PERITONEAL MEMBRANE PLASMAPHERESIS

This application is a continuation of application Ser. No. 874,793, filed June 13, 1986, now abandoned, which is a continuation of application Ser. No. 817,155, filed Jan. 7, 1986, now abandoned, which is a continuation of Ser. No. 540,010, filed Oct. 7, 1983, now abandoned.

BACKGROUND OF THE INVENTION

The present invention relates to a method of medical treatment of a patient for diseases related to plasma proteins, and referred to as plasmapheresis.

To appreciate the nature of the present invention, a brief discussion of the makeup of blood is useful. Approximately 45% of the volume of blood is in the form of cellular components. These cellular components include red cells, also referred to as erthrocytes, white cells, also referred to as leukocytes, and platelets. Plasma makes up the remaining 55% of the volume of blood. Basically, plasma is the fluid portion of the blood which suspends the cells and comprises a solution of approximately 90% water, 7% protein and 3% of the various other organic and inorganic solutes.

In the past twenty years, a group of diseases have been identified which are mediated by circulating proteins and subgroups of proteins called antibodies. Many of these disease processes, for which the etiology has not been determined, have been classified as antibody-mediated diseases. An incomplete list of diseases which fall into this category would include: (1) systemic lupus erythematosus, (2) Guillain-Barre Syndrome, (3) myasthenia gravis, (4) polymyositis, (5) acute and chronic glomerulonepbritis, (6) Goodpasture's syndrome, (7) polyarteritis nodosa, (8) thrombotic thrombocytopenic purpura, (9) Waldenstrom's macroglobulinemia, (10) scleroderma, (11) rheumatoid arthritis, (12) multiple sclerosis, (13) rheumatic fever, and (14) transplant rejection.

Manipulation of the production of proteins and, therefore, antibodies, became possible with the isolation and production of cortisone. This hormone and its synthetic derivatives are presently used to decrease the production and reaction of the harmful antibodies produced in the above-mentioned disease processes. Other non-cortisone drugs (immunosuppressants) first developed as cancer chemotherapy are also used to decrease the production of these antibodies. Both cortisone and immunosuppressive drugs have substantial risks and side-effects, but are presently used as the first line approach in the treatment of diseases related to antibody production.

In the late 1950's and early 1960's, it was discovered that mechanical removal of abnormal antibodies in certain disease processes could be beneficial. This was first used in the treatment of Waldenstrom's macroglobulinemia, a disease in which an abnormal protein of very large size (one million molecular weight) is produced. As the concentration of this abnormal protein increases, the blood becomes extremely viscous, producing a syndrome called hyperviscosity syndrome.

During this same period, many of the aforementioned disease processes were identified as being mediated by circulating proteins. Interest arose in the possible clinical effects of protein removal from whole blood, also known as plasmapheresis. Parallel with the development of the plasmapheresis concept was the development of sophisticated blood banking in which component therapy was defined (i.e., isolation of platelets and white blood cells, red blood cell separation, washing, storing and freezing). These new therapeutic modalities stimulated the development of technology to rapidly separate the plasma component of whole blood from the cellular components.

Separation of blood into a plasma fraction and a cellular component fraction is desirable for many medical reasons. For example, separation of blood into plasma fractions and cellular component fractions provides for a collection of plasma alone, with the cellular components being returned to the donor with a suitable portion of replacement fluid. This process is broadly referred to as "plasmapheresis." Thus, plasmapheresis provides for the collection of plasma from donors without the removal of the cellular components from the diseased plasma and returning the cellular components to the patient in admixture with a suitable replacement fluid, or by further fractionating the patient's plasma to remove the unwanted substances and returning a major portion of the patient's plasma with the cellular components. Finally, a plasmapheresis process can be employed for diagnostic purposes wherein plasma is separated from the cellular components and analyzed to detect disease-causing substances or conditions therein.

Heretofore, plasmapheresis has been accomplished primarily by removal of a quantity of blood from a patient, separating the cellular component from the plasma component and returning the cellular component to the patient. In some cases, replacement of the removed plasma is required. In a manual method of plasmapheresis, the desired amount of blood is removed by venipuncture. The cellular components are separated from the plasma component by a centrifuge. The plasma portion is manually removed from the centrifuge, and the cellular component is returned to the patient. Fresh plasma or a fluid supplement is returned to the patient along with the cellular component as a replacement for the separated plasma.

Plasmapheresis has also been conducted by a cell separator method. In this process, circulatory access to a patient is achieved. Instrumentation connected to the patient provides either continuous flow centrifugation or intermittent flow centrifugation. In continuous flow centrifugation, a quantity of blood is removed to a centrifugal element. Blood centrifugal and plasma are removed by a peristaltic pump to a collection container. From there, the cellular component of the blood and replacement fluid are returned to the patient. In intermittent flow centrifugation, a quantity of blood is removed to a centrifugal element by a blood pump. Operation of the centrifuge is intermittently discontinued to retrieve the cellular component, which is returned to the patient along with replacement fluids. The separated plasma is drained to a waste collection container.

Another method of plasmapheresis involves the use of an external membrane. Circulatory access to the patient is achieved and attachment is made to instrumentation including a pair of blood pumps and a plasma separator comprising a membrane. The blood removed from the patient is introduced to a membrane cell separator. Cellular components of the blood are rejected from the membrane with plasma being filtered through. The plasma is returned to a waste collection container. The cellular component is returned to the patient along with the replacement fluid.

In summary, plasmapheresis as it has heretofore been practiced involves taking blood from the body, and passing it into a separation device which separates the plasma from cellular aspects. Two things can happen then. One is to throw away the plasma, replace it with a substitute plasma, and reinfuse this into the body. By this procedure, it is possible to replace the plasma of the body, which is useful in a large number of disease states, mainly those which are manifested by the presence of large protein molecules in the body which have very adverse clinical effects. Alternatively, the offending molecules are removed from the plasma. Then, the same plasma is put back into the line and returned to the body. The separation can be made by means of centrifuge or by means of membrane filtration.

The present invention provides an alternative procedure for accomplishing plasmapheresis.

SUMMARY OF THE INVENTION

The procedure of the present invention is referred to herein in a short-hand phrase of "Peritoneal Membrane Plasmapheresis" (PMP), and refers to protein removal from the blood vascular space through the peritoneal membrane. The phrase derives from the word "plasmapheresis" which refers to the separation of plasma from whole blood in order to remove offending substances, and from the fact that use is made of the peritoneal membrane. The peritoneal membrane is a semipermeable membrane located in the abdominal cavity. The present invention realizes that through the manipulation of the dynamics of mass transfer across the peritoneal membrane, protein molecules can be removed from the blood in a manner so as to effect plasmapheresis treatment of a patient.

PMP allows patients to perform protein removal treatment at home at considerably less expense than prior art techniques. It is a form of self care that provides a more gentle protein removal without necessitating long term vascular access or rapid vascular depletion. One of the advantageous aspects is that there is provided continuous protein removal. That is, instead of rapid intermittent protein removal as heretofore done, plasma removal occurs continuously.

The method of this invention involves the infusion and drainage on a prescribed schedule of an irrigating fluid (hereinafter referred to as "plasmate") containing a vasoactive drug. The objective is to achieve removal of large protein molecules.

DETAILED DESCRIPTION OF THE INVENTION

I. Introductory Plasmapheresis Principles

The peritoneum is the largest serous membrane of the body. It lines the inside of the abdominal wall (the parietal peritoneum) and is reflected over the viscera (the visceral peritoneum). The space between the parietal and visceral portions of the membrane is called the peritoneal cavity. This is normally a potential space lubricated by serous fluid secreted by mesothelial cells which cover its free surface.

The microscopic anatomy of the peritoneum consists of five layers of fibrous and elastic connective tissue covered by mesothelial cells. Blood and lymphatic capillaries are located in the deepest layers in adults. Thus, for a substance to pass from the bloodstream into the peritoneal cavity, it must pass the capillary endothelium, the interstitium, the mesothelium and any fluid film resistances.

II. The PMP Method

The PMP method generally involves a process of removing proteins from the blood vascular space through the peritoneal cavity. The mechanism of protein removal through the peritoneal membrane is that of mass transfer dynamics involving solute diffusion due to plasma-plasmate gradient and convection due to water movement out of plasma. As to the diffusion transport mechanism, plasmate placed in the peritoneal cavity moves toward concentration equilibrium, with plasma. As to the convection mechanism, net osmotic and hydrostatic forces are at work to promote the movement of water out of plasma. The diffusion mechanism is a matter of random kinetic movement of protein molecules, which attempt to evenly distribute throughout the space available. The convection mechanism is a matter of transperitoneal fluid shifts (ultrafiltration) which drag protein molecules through the membrane. An integral part of the protein removal process in accordance with the PMP method involves manipulation of the plasmate by addition of a vasoactive drug and the schedule of plasmate infusion/drainage (i.e., "exchanges"). The result is maximum clearances of large molecular weight proteins.

Generally, in the PMP method, plasmate containing a vasoactive drug is infused into the peritoneal cavity. After a prescribed residence time period, the plasmate is drained and fresh plasmate is infused. Preferred vasoactive drugs include histamine phosphate, sodium nitroprusside, dipyridamole, and dibenzyline. Histamine phosphate is a diagnostic tool used for hyposensitivity therapy, pheochromacytoma and gastic secretion treatment. Sodium nitroprusside is a rapid acting, intravenous antihypertensive agent. Dipyridamole is a coronary vasodilator. These drugs may be used singly or in combination.

III. Determination of Optimum Exchange Schedule

To evaluate the removal of proteins via peritoneal membrane plasmapheresis, PMP, some basis is required to establish a plasmate exchange schedule which is equivalent to that which has been demonstrated to be effective using standard plasmapheresis methods. Conventional plasmapheresis treatment using centrifugal or external membrane methodology is highly intensive and intermittent in character. Treatments are usually applied one or more times per week over a time period usually extending from 2 to 5 hours. The patient is then disconnected from the machinery followed by a gradual build up of the toxin protein molecules within the patient.

The blood concentration of proteins is defined under any set of circumstances by the following general field equation:

$$\frac{d(VC)}{dt} = -KC + G \qquad (1)$$

where:
 C = toxic protein concentration level
 V = protein volume of distribution
 K = protein clearance rate
 G = protein generation rate This equation can be solved for the protein build up between standard plasmapheresis treatments as follows.

Between treatments, $K = 0$ and $V = $ constant. Therefore, equation (1) reduces to:

$$V \frac{dC}{dt} = G \quad (2)$$

This equation can be solved for the protein concentration by integration between the initial concentration at the end of the previous plasmapheresis treatment, $C_o$, and the highest protein concentration level, $C_1$, immediately prior to the next plasmapheresis treatment during the time interval of t.

$$\int_{C_o}^{C_1} dC = \int_0^{\Delta t} \frac{G}{V} dt \quad (3)$$

This yields:

$$C_1 - C_0 = \frac{G}{V} \Delta t \quad (4)$$

$C_o$ can be expressed in terms of $C_1$ as follows:

$$C_o = BC_1 \quad (5)$$

which yields:

$$C_1(1-B) = \frac{G}{V} \Delta t \quad (6)$$

Note that (1 - B) is the degree of efficiency of the plasma-pheresis treatment and varies between 0 and 1.0 (100% efficient). Substitution of $\phi$ for (1-B) yields an expression for $C_1$.

$$C_1 = \frac{G}{V} \frac{\Delta t}{\phi} \quad (7)$$

where:
$C_1$ = preplasmapheresis protein concentration level
$G$ = protein generation rate
$\Delta t$ = time period between plasmapheresis treatments
$\phi$ = efficiency of plasmapheresis treatment This equation can be compared to a comparable equation defining the protein concentration level using PMP. Assuming the protein removal rate during PMP is essentially continuous, $d(VC)/dt=0$ in the general field equation. For these circumstances, equation (1) can be directly solved to yield (during PMP):

$$C = \frac{G}{K}$$

It is the high concentrations of toxic protein molecules which give rise to clinical pathology. Thus, the maximum acceptable PMP protein concentration level is $C_1$ (the preplasmapheresis level with standard treatment modalities). This yields:

$$C_1 = \frac{G}{K_1}$$

where $K_1$ = PMP clearance required to maintain the protein concentration level at $C_1$.

Equations (7) and (9) are written in terms of the same value for $C_1$. Thus they can be equated to yield:

$$\frac{G}{K_1} = \frac{G}{V} \frac{\Delta t}{\phi}$$

Since G appears on both sides of the equation and can be cancelled, solving for $K_1$ gives:

$$K_1 = \frac{V}{\Delta t} \phi \quad (11)$$

This defines the PMP clearance required to achieve the same preplasmapheresis protein concentration level using conventional techniques.

PMP clearance, $K_1$, is in turn defined by the protein removal rate divided by the concentration level in the blood.

$$K_1 = \frac{V_D C_D}{tC} \quad (12)$$

where:
$V_D$ = drained plasmate volume
$C_D$ = protein concentration level in drained plasmate
$t$ = time between PMP exchanges
$C$ = protein concentration level in blood Again, both equations (11) and (12) are written in terms of the same value of $K_1$. Equating these and solving for $\Delta t$ yields the desired expression.

$$\Delta t = \frac{V}{V_D} \cdot \frac{C}{C_D} \cdot t \cdot \phi \quad (13)$$

which can be written to solve for t as:

$$t = \frac{V_D C_D}{VC \phi} \Delta t \quad (14)$$

Equation (13) predicts the time between conventional plasmapheresis treatments which will yield the same maximum value of blood protein concentration level for a given set of PMP data.

For example, assume the following data was obtained for a two liter infusion of plasmate containing 2.0 mg Histamine Phosphate in a canine:
$V_D$ = 2250 ml drained plasmate
$C_D$ = 47 mg/dl total protein in drained plasmate
$t$ = 2 hour dwell period
$C$ = 5,800 mg/dl blood total protein level (5.8% protein)

The volume of distribution, V, can be estimated as the plasma volume which is approximately 4% of the canine weight of 18.18 Kg.

$V = 0.04 \times 18,180 = 727$ ml plasma volume

Conventional plasmapheresis treatments are approximately 80% efficient (i.e. 80% of circulating proteins are replaced by fresh plasma proteins during the treatment). Therefore = 0.8.

Substitution of these values into equation (13) yields:

$$t = \frac{727}{2250} \times \frac{5800}{47} \times 2 \times 0.8 = 63.8 \text{ hours}$$

or t=2.66 days.

This states that if plasma proteins were continuously removed at the rate illustrated, this would be equivalent to performing a conventional plasmapheresis treatment once every 2.66 days.

IV. PMP Clinical Protocol

To prepare a patient for PMP treatment, a peritoneal catheter is surgically implanted into the peritoneal cavity. Then, postoperatively and using a sterile technique, access tubing is attached to the catheter. Using an aseptic technique, a container of sterile isotonic or heparinized solution of 500–1000 ml is attached to the catheter access tubing. Irrigations are conducted two to three times daily until the effluent clears. The irrigation solution may be changed as frequently as desired but should be changed at least once daily.

To provide the fluid for infusion into the peritoneal cavity, a container of plasmate having added to it the appropriate vasoactive drug(s) is used. Preferably, the plasmate container is a plastic bag, and the vasoactive drug agent is added to the bag by injection. The procedure for adding the vasoactive drug to the dialysis solution bag should be made in a manner that reduces contamination.

The plasmate containing the vasoactive drug(s) is infused into the peritoneal cavity and allowed to remain there for the prescribed dwell time period, after which it is drained. Fresh plasmate with the vasoactive drug(s) is then infused.

A modification of this protocol is to intermittently add vasoactive drugs at prescribed time periods during a long dwell period. This is accomplished by draining a small volume of plasmate into an attached container at prescribed time intervals. Additional vasoactive drugs are injected into the small volume of plasmate and reinfused into the peritoneal cavity. This process is repeated as often as required.

V. PMP Clinical Results

Clinical results discussed herein will be presented in terms of an equivalence index. This index represents the number of days between standard plasmapheresis treatments which would be equivalent to the protein removal rate observed on PMP on a continuous basis (See Section III).

The effects of dwell time on the equivalence index is presented in Table I. In studies performed, 9 mg of Nitroprusside and 2 mg of Histamine Phosphate in 2 liters of 1.5% Dianeal was used with canine subjects. As shown in Table I, the equivalence index decreases dramatically with decreasing dwell time. The equivalence index approaches clinical efficacy (in the range of 3.5-7 days) for dwell times less than seven hours for the medications indicated. The low equivalence index of 4.7 days for a two hour dwell period demonstrates that multiple or continuous drug infusions are desirable.

TABLE I

| EFFECT OF DWELL TIME (9 mg NP & 2 mg HP) | |
|---|---|
| Dwell Time (hours) | Equivalence Index (days) |
| 2 | 4.7 |
| 7 | 8.0 |
| 17 | 29.5 |

Multiple drug infusions can be accomplished utilizing either fresh or continuous dwelling plasmate. Studies made included the use of 2 mg of Histamine Phosphate per drug infusion. In the first case, the plasmate was drained following each two hour dwell period followed by infusion of fresh plasmate with 2 mg Histamine Phosphate. This resulted in the average equivalence index of 5.7 days. In the second case, 100 ml of plasmate was withdrawn after two hours. Two mg Histamine Phosphate was added to this solution followed by reinfusions; this was repeated twice. The same equivalence index was obtained, demonstrating that the same plasmate may be utilized for an extended time period with repeated or continuous drug infusions.

Technical analyses suggest that plasmate may be utilized with continuous or multiple, intermittent drug infusion until the protein level in the plasmate approaches approximately 25% of that in the blood. At this point the diffusive gradient between blood and plasmate will be reduced to $\frac{3}{4}$ of the initial value, with a proportional decrease in the rate of protein transport. At some point (approaching 50% of equivalence) fresh plasmate needs to be utilized to maintain adequate protein removal rates.

The effect of Histamine Phosphate concentration levels is illustrated in table II. Histamine Phosphate concentrations of 0, 2, 3, and 4 mg per 2 liter infusion are presented. The equivalence index is illustrated in each instance with several dwell periods. Table II shows that clinically acceptable equivalence indexes can be obtained with low Histamine Phosphate concentrations and short dwell times (2 hours), or with high concentrations of Histamine Phosphate (4 mg) and longer dwell times.

TABLE II

| EFFECT OF HISTAMINE PHOSPHATE CONCENTRATION | | | |
|---|---|---|---|
| | Equivalence Index (days) | | |
| Histamine Phosphate Concentration (mg) | 2 hr dwell | 7 hr dwell | 17 hr dwell |
| Control | | 39.4 | 48.9 |
| 2.0 | 4.9 | 8.0 | 29.5 |
| 3.0 | | 8.5 | 20.2 |
| 4.0 | | 4.2 | 10.2 |

The effect of Nitroprusside concentration in conjunction with Histamine Phosphate is illustrated in Table III. All exchanges include 2 mg Histamine Phosphate with two hour dwell times. It is seen that the equivalence indexes without Nitrorusside are only slightly greater than those containing 9 mg of Nitroprusside. This illustrates that Histamine Phosphate exhibits the dominant vasoactive effect under these circumstances.

TABLE III

| EFFECT OF NITROPRUSSIDE CONCENTRATION (Three exchanges with 2 mg HP every 2 hrs) | | |
|---|---|---|
| | Equivalence Index - days | |
| Exchange | Without NP | With 9 mg NP |
| 1 | 6.4 | 4.0 |
| 2 | 5.1 | 5.4 |
| 3 | 5.0 | 4.8 |

The effect of Dibenzyline is illustrated in Table IV. Twenty-five mg of Dibenzyline was injected into 2,000 ml 1.5% Dianeal with a two hour dwell period. An equivalence index (EI) of 0.68 days was obtained. This is equivalent to performing a standard plasmapheresis treatment approximately daily and may be an excellent method to begin the PMP protocal with later switching to a drug with longer equivalence indexes. Dibenzyline is the most potent PMP agent presently known.

TABLE IV
EFFECT OF DIBENZYLINE
*2.0 liters 1.5 gm % Dextrose Dianeal
*2 hour dwell time
*25 mg Dibenzyline added to Dianeal
EI (control) = 120 days
EI (Dibenzyline) = 0.68 days A single PMP clinical study with humans was performed. The effects of Dypyridamole in a patient were tested. Dypyridamole 75 mg was administered orally, three times daily with four plasmate exchanges daily with a four hour dwell period. The results are presented in Table V. Equivalence indexes ranging from 2.8 to 12.6 days were obtained with a 6.5 day average value. This suggests that Dypyridamole may be an effective PMP pharmacological agent in an adult male.

TABLE V
DIPYRIDAMOLE - PATIENT
*75 mg orally three times daily
*4 hour dwell, 2.5 mg % Dianeal
Control EI = 42 days
PMP EI = 2.8 to 12.6 days
(6.5 average)

Overall, the clinical results demonstrate that PMP is a viable, clinical concept. Protein removal rates sufficiently high to be equivalent with standard external membrane and centrifuge techniques can be obtained. Specific protein removal rates can be optimized by variations in drug concentration and dwell times to conform to clinical requirements as outlined in Section III.

An alternative approach to performing the peritoneal membrane plasmapheresis method of the present invention would be for the patient to attach himself, for example during the evening hours while sleeping, to apparatus that provides fresh plasmate solution and the necessary vasoactive drug infusions. The patient could maintain a residual plasmate volume during the day when awake, or could completely drain the peritoneal cavity and rely solely upon the protein removal accomplished during the evening hours.

The foregoing description of the invention has been directed to particular examples and preferred techniques for purposes of explanation and illustration. It will be apparent, however, to those skilled in this art that modifications and changes may be made without departing from the essence of the invention. It is the applicants' intention in the following claims to cover all equivalent modifications and variations as fall within the scope of the invention.

What is claimed is:

1. A method of protein removal in the treatment of a patient having a protein mediated disease, comprising the steps of:
    infusing plasmate containing a vasoactive drug into the peritoneal cavity;
    allowing the plasmate to remian in the peritoneal cavity for a predetermined dwell time period sufficient to effect removal of circulating portein molecules from the blood vascular space of the body of substantially equivalent size and at a substantially equivalent removal rate to the protein removal achieved through extracorporeal plasmapheresis treatment; and
    draining the plasmate from the peritoneal cavity.

2. The method of claim 1 further comprising the step of:
    intermittently adding vasoactive drugs at predetermiend points in time during the dwell time period.

3. The method of claim 1 further comprising the step of:
    continuously adding vasoactive drugs at predetermined points in time during the dwell time period.

4. The method of claim 1 wherein the vasoactive drug is chosen from a group consisting of:
    dipyridamole, sodium nitroprusside, histamin phosphate and dibenzyline.

5. The method of claim 1 further comprising the step of:
    infusing fresh plasmate containing a vasoactive drug into the peritoneal cavity.

6. The method of claim 1 wherein the dwell time period is detemined from the equation:

$$t = \frac{V_D C_D}{VC \phi} \Delta t$$

t = dwell time for infused plasmate
where:
  $\Delta t$ = time period between treatments in a conventional plasmapheresis protocol to be approximated by PMP
  V = protein volume of distribution
  C = toxic protein concentration level
  $V_D$ = volume of plasmate previously drained
  $C_D$ = protein concentration level in drained plasmate
  $\phi$ = efficiency rate

* * * * *